United States Patent
Higashiyama et al.

(10) Patent No.: US 11,660,275 B2
(45) Date of Patent: May 30, 2023

(54) EPILEPSY TREATMENT AGENT

(71) Applicant: Eisai R&D Management Co., Ltd., Tokyo (JP)

(72) Inventors: Hiroyuki Higashiyama, Kamakura (JP); Hisashi Wakita, Tsukuba (JP); Yoshimasa Ito, Wynnewood, PA (US); Yoshihide Osada, Kawasaki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/975,865

(22) PCT Filed: Mar. 18, 2019

(86) PCT No.: PCT/JP2019/011184
§ 371 (c)(1),
(2) Date: Aug. 26, 2020

(87) PCT Pub. No.: WO2019/181854
PCT Pub. Date: Sep. 26, 2019

(65) Prior Publication Data
US 2021/0000771 A1    Jan. 7, 2021

(30) Foreign Application Priority Data

Mar. 20, 2018   (JP) .............................. JP2018-052974

(51) Int. Cl.
| A61K 31/18 | (2006.01) |
| A61K 31/4375 | (2006.01) |
| A61K 31/444 | (2006.01) |
| A61K 31/506 | (2006.01) |

(52) U.S. Cl.
CPC .......... *A61K 31/18* (2013.01); *A61K 31/4375* (2013.01); *A61K 31/444* (2013.01); *A61K 31/506* (2013.01)

(58) Field of Classification Search
CPC .. A61K 31/18; A61K 31/4375; A61K 31/444; A61K 31/506
See application file for complete search history.

(56) References Cited

U.S. PATENT DOCUMENTS

| 3,383,414 | A | 5/1968 | Houlihan |
| 3,709,677 | A | 1/1973 | Houlihan |
| 4,820,705 | A | 4/1989 | Nickl et al. |
| 6,958,416 | B2 | 10/2005 | Bialer et al. |
| 2004/0072880 | A1 | 4/2004 | Lloyd et al. |
| 2005/0014845 | A1 | 1/2005 | Gaida et al. |
| 2005/0234106 | A1 | 10/2005 | Lloyd et al. |
| 2006/0047001 | A1 | 3/2006 | Parker et al. |
| 2007/0142333 | A1 | 6/2007 | Lloyd et al. |
| 2007/0142640 | A1 | 6/2007 | Arimoto et al. |
| 2007/0155823 | A1 | 7/2007 | Smith-Swintosky et al. |
| 2011/0092539 | A1 | 4/2011 | Gillespie et al. |
| 2012/0077814 | A1 | 3/2012 | Wang et al. |
| 2012/0202781 | A1 | 8/2012 | Gillen et al. |
| 2012/0302546 | A1 | 11/2012 | Smith et al. |
| 2014/0024650 | A1 | 1/2014 | Fukumoto et al. |
| 2014/0371319 | A1 | 12/2014 | Kazuta et al. |
| 2016/0303058 | A1 | 10/2016 | Higashiyama et al. |
| 2017/0137436 | A1 | 5/2017 | Kurokawa et al. |

FOREIGN PATENT DOCUMENTS

| CL | 200502009 | 4/2006 | |
| CL | 200502131 | 5/2006 | |
| CL | 200502130 | 8/2006 | |
| CL | 200701467 | 3/2008 | |
| CL | 200701468 | 4/2008 | |
| CL | 4598397 | 12/2010 | |
| CN | 1807419 | 7/2006 | |
| CN | 101090896 | 12/2007 | |
| CN | 102365265 | 2/2012 | |
| CN | 104395285 | 3/2015 | |
| CN | 105848656 | 8/2016 | |
| EP | 2865663 | 4/2015 | |
| JP | 2006-508016 | 3/2006 | |
| JP | 2009-513549 | 4/2009 | |
| JP | 2011-523656 | 8/2011 | |
| JP | 2012-523393 | 10/2012 | |
| JP | 2014-523851 | 9/2014 | |
| MX | PA04007365 | 3/2005 | |
| RU | 2010119646 | 11/2011 | |
| RU | 2619937 | 5/2017 | |
| WO | WO 2003/063797 | 8/2003 | |
| WO | WO 2006/004100 | 1/2006 | |
| WO | WO 2007/075698 | 7/2007 | |
| WO | WO 2009/050252 | 4/2009 | |
| WO | WO 2009/147167 | 12/2009 | |
| WO | WO 2010/115952 | 10/2010 | |
| WO | WO 2011/060391 | 5/2011 | |
| WO | WO 2011/060392 | 5/2011 | |
| WO | WO 2013/191144 | 12/2013 | |
| WO | WO-2013191144 A1 * | 12/2013 | ............. A61K 31/18 |
| WO | WO 2015/093515 | 6/2015 | |
| WO | WO 2017/082288 | 5/2017 | |

OTHER PUBLICATIONS

Dr. Jennifer Frank, "Managing Hypertension Using Combination Therapy." American Academy of Family Physicians. (2008); 77(9): 1279-1286, 1289 (Year: 2008).*

Hanada, et al. "Effect of perampanel, a novel AMPA antagonist, on benzodiazepine-resistant status epilepticus in a lithium-pilocarpine rat model." Pharmacology Research and Perspectives. (2014), vol. 2(5), pp. 1-8 (Year: 2014).*

"Managing Hypertension Using Combination Therapy." AAFP. 2008 (Year: 2008).*

(Continued)

*Primary Examiner* — John S Kenyon
*Assistant Examiner* — Gillian A Hutter
(74) *Attorney, Agent, or Firm* — Fish & Richardson P.C.

(57) ABSTRACT

Provided is a combination agent that combines N-[(1S)-2,2,5,7-tetrafluoro-2,3-dihydro-1H-inden-1-yl]sulfamide with an AMPA-type glutamate receptor antagonist such as 3-(2-cyanophenyl)-5-(2-pyridyl)-1-phenyl-1,2-dihydropyridin-2-one or 2-fluoro-6-(3-fluoro-8-oxo-7-(pyridin-3-yl)-7,8-dihydro-6H-pyrano[3,2-b:5,4-b']dipyridin-9-yl)benzonitrile, and it has potential for use as a therapeutic agent for epilepsy.

5 Claims, 2 Drawing Sheets

(56) References Cited

OTHER PUBLICATIONS

Office Action in Russian Patent Application No. 2020128731, dated Dec. 9, 2021, 20 pages (with English Translation).
Official Notification in European Patent Application No. 19772593.0, dated Nov. 5, 2021, 1 page.
Office Action in Singaporean Patent Application No. 11202007200Y, dated Apr. 15, 2021, 8 pages.
Search Report in European Patent Application No. 19772593.0, dated Oct. 18, 2021, 13 pages.
Notice of Allowance in Singaporean Patent Application No. 11202007200Y, dated Jun. 17, 2021, 6 pages.
Office Action in Israeli Patent Application No. 276966, dated Apr. 22, 2021, 5 pages (with English Translation).
Submission Document in Singaporean Patent Application No. 11202007200Y, dated Jun. 8, 2021, 36 pages.
Submission Document in Israeli Patent Application No. 276966, dated Aug. 17, 2021, 5 pages (with English Translation).
Das et al., "An overview on antiepileptic drugs," Drug Discoveries & Therapeutics, 2012, 6(4):178-193.
Hanada et al., "Effect of perampanel, a novel AMPA antagonist, on benzodiazepine-resistant status epilepticus in a lithium-pilocarpine rat model," Pharmacology Research & Perspectives, 2014, 2(5):1-8.
PCT International Preliminary Report on Patentability in International Appln. No. PCT/JP2019/011184, dated Oct. 1, 2020, 9 pages.
PCT International Search Report in International Appln. No. PCT/JP2019/011184, dated Jun. 4, 2019, 2 pages.
Schidlitzki et al., "A combination of NMDA and AMPA receptor antagonists retards granule cell dispersion and epileptogenesis in a model of acquired epilepsy," Scientific Reports, Sep. 2017, 7(12191):1-19.
Notice of Allowance in Australian Patent Application No. 2013278450, dated Apr. 11, 2017, 3 pages.
Notice of Allowance in Canadian Patent Application No. 2877097, dated Mar. 28, 2018, 1 page.
Notice of Allowance in Chilean Patent Application No. 2014-03429, dated Nov. 15, 2018, 14 pages (with English Translation).
Notice of Allowance in Chinese Patent Application No. 201380031833.8, dated Feb. 2, 2016, 4 pages (with English Translation).
Notice of Allowance in European Patent Application No. 13807707.8, dated Mar. 9, 2017, 2 pages.
Notice of Allowance in Golf Cooperation Council Patent Application No. 24703/2013, dated Jan. 2, 2017, 2 pages (with English Translation).
Notice of Allowance in Indonesian Patent Application No. P-00201500287, dated Nov. 5, 2019, 5 pages (with English Translation).
Notice of Allowance in Israeli Patent Application No. 236295, dated Jul. 5, 2016, 5 pages (with English Translation).
Notice of Allowance in Japanese Patent Application No. P2014-521462, dated Feb. 2, 2016, 5 pages (with English Translation).
Notice of Allowance in Jordanian Patent Application No. 184/2013, dated Apr. 16, 2018, 2 pages (with English Translation).
Notice of Allowance in Korean Patent Application No. 10-2014-7035140, dated Jan. 21, 2019, 5 pages (with English Translation).
Notice of Allowance in Malaysian Patent Application No. PI2014703797, dated Aug. 30, 2018, 3 pages.
Notice of Allowance in Mexican Patent Application No. MX/a/2014/015492, dated Feb. 6, 2018, 3 pages (with English Translation).
Notice of Allowance in New Zealand Patent Application No. 702974, dated Mar. 24, 2016, 1 page.
Notice of Allowance in Russian Patent Application No. 2014151013, dated Jan. 18, 2017, 17 pages (with English Translation).
Notice of Allowance in Singaporean Patent Application No. 11201408359P, dated Mar. 8, 2017, 4 pages.
Notice of Allowance in South African Patent Application No. 2014/09248, dated Oct. 12, 2015, 3 pages.
Notice of Allowance in Taiwanese Patent Application No. 102122236, dated Jun. 7, 2017, 5 pages (with English Translation).
Notice of Allowance in Ukrainian Patent Application No. a201413560, dated Apr. 28, 2016, 9 pages (with English Translation).
Notice of Allowance in Vietnamese Patent Application No. 1-2014-04194, dated Sep. 25, 2017, 8 pages.
Office Action in Argentine Patent Application No. P130102174, dated Oct. 8, 2019, 4 pages (with English Translation).
Office Action in Australian Patent Application No. 2013278450, dated Oct. 31, 2016, 2 pages.
Office Action in Brazilian Patent Application No. BR112014031565-5, dated Jan. 21, 2020, 8 pages (with English Translation).
Office Action in Canadian Patent Application No. 2877097, dated Feb. 7, 2018, 3 pages.
Office Action in Chilean Patent Application No. 2014-03429, dated Feb. 9, 2016, 13 pages (with English Translation).
Office Action in Chilean Patent Application No. 2014-03429, dated May 30, 2016, 10 pages.
Office Action in Chinese Patent Application No. 201380031833.8, dated Jul. 16, 2015, 10 pages (with English Translation).
Office Action in Indian Patent Application No. 9043/CHENP/2014, dated Sep. 5, 2018, 4 pages (with English Translation).
Office Action in Indonesian Patent Application No. P-00201500287, dated Apr. 8, 2019, 4 pages.
Office Action in Indonesian Patent Application No. P-00201500287, dated Nov. 6, 2018, 4 pages (with English Translation).
Office Action in Israeli Patent Application No. 236295, dated Aug. 27, 2015, 5 pages (with English Translation).
Office Action in New Zealand Patent Application No. 702974, dated Dec. 15, 2015, 2 pages.
Office Action in Pakistani Patent Application No. 409/2013, dated Jul. 23, 2015, 3 pages.
Office Action in Peruvian Patent Application No. 002429-2014, dated Jun. 2, 2017, 3 pages (with English Translation).
Office Action in Peruvian Patent Application No. 002429-2014, dated Oct. 9, 2018, 19 pages (with English Translation).
Office Action in Philippine Patent Application No. 1-2014-502805, dated Mar. 2, 2016, 2 pages.
Office Action in Taiwanese Patent Application No. 102122236, dated Oct. 27, 2016, 5 pages (with English Translation).
Official Notification in Israeli Patent Application No. 236295, dated Sep. 29, 2016, 1 page (with English Translation).
Quan et al., "Preparation of 4,5-dihydro-1,2,4-triazolo[4,3-a]quinolin-1-one derivatives as antiepileptic agents," Chemical Abstracts Service, Columbus, Ohio, US, 2006, XP002752667, 1 page.
Submission Document in Argentine Patent Application No. P130102174, dated Nov. 14, 2019, 7 pages (with English Translation).
Submission Document in Australian Patent Application No. 2013278450, dated Feb. 28, 2017, 16 pages.
Submission Document in Brazilian Patent Application No. BR112014031565-5, dated Apr. 13, 2020, 20 pages (with English Translation).
Submission Document in Canadian Patent Application No. 2877097, dated Mar. 6, 2018, 8 pages.
Submission Document in Chilean Patent Application No. 2014-03429, dated Apr. 5, 2016, 124 pages (with English Translation).
Submission Document in Chilean Patent Application No. 2014-03429, dated Aug. 5, 2016, 14 pages (with English Translation).
Submission Document in Chinese Patent Application No. 201380031833.8, dated Oct. 9, 2015, 15 pages (with English Translation).
Submission Document in Indian Patent Application No. 9043/CHENP/2014, dated Mar. 1, 2019, 7 pages.
Submission Document in Indonesian Patent Application No. P-00201500287, dated Feb. 6, 2019, 3 pages (with English Translation).
Submission Document in Indonesian Patent Application No. P-00201500287, dated Jul. 4, 2019, 4 pages (with English Translation).
Submission Document in Israeli Patent Application No. 236295, dated Dec. 17, 2015, 2 pages (with English Translation).
Submission Document in New Zealand Patent Application No. 702974, dated Feb. 25, 2016, 14 pages.
Submission Document in Peruvian Patent Application No. 002429-2014, dated Jun. 7, 2017, 2 pages (with English Translation).

(56) References Cited

OTHER PUBLICATIONS

Submission Document in Peruvian Patent Application No. 002429-2014, dated Nov. 27, 2017, 9 pages (with English Translation).
Submission Document in Philippine Patent Application No. 1-2014-502805, dated Mar. 29, 2016, 7 pages.
Submission Document in Taiwanese Patent Application No. 102122236, dated Jan. 25, 2017, 17 pages (with English Translation).
Office Action in Indian Patent Application No. 202047037166, dated Mar. 14, 2022, 6 pages (with English Translation).
Sarhan et al., "Evidence for efficacy of combination of antiepileptic drugs in treatment of epilepsy," Journal of Neurology Research, 2016, 5(6):267-276.
Submission Document in European Patent Application No. 19772593.0, dated Feb. 7, 2022, 21 pages.
Office Action in Mexican Patent Application No. MX/a/2020/009100, dated Apr. 11, 2022, 9 pages (with English Translation).
Office Action in Chinese Patent Application No. 201980016269.X, dated Oct. 31, 2022, 17 pages (with English Translation).
Yu et al., "Perampanel," Drug & Clinic, 2011, 26(4):330-332 (with English Abstract).
Submission Document in Mexican Patent Application No. MX/a/2020/009100, Aug. 11, 2022, 11 pages.
Office Action in Mexican Patent Application No. MX/a/2020/009100, dated Nov. 30, 2022, 5 pages (with English Translation).
Office Action in Japanese Patent Application No. P2020-507787, dated Jan. 4, 2023, 7 pages (with English Translation).
Official Notification in Australian Patent Application No. 2019239394, dated Jan. 4, 2023, 1 page.
Submission Document in Chinese Patent Application No. 201980016269.X, dated Feb. 2, 2023, 42 pages (with English Translation).
Office Action in Chinese Patent Application No. 201980016269.X, dated Mar. 8, 2023, 11 pages (with English Translation).
Notice of Allowance in Japanese Patent Application No. P2020-507787, dated Apr. 11, 2023, 6 pages (with English Translation).

* cited by examiner

Fig.2

EPILEPSY TREATMENT AGENT

TECHNICAL FIELD

The present invention relates to a therapeutic agent for epilepsy that combines an indan-1-ylsulfamide derivative and an AMPA-type glutamate receptor antagonist. More specifically, it relates to a therapeutic agent for epilepsy that combines N-[(1S)-2,2,5,7-tetrafluoro-2,3-dihydro-1H-inden-1-yl]sulfamide (or a pharmaceutically acceptable salt thereof) and an AMPA-type glutamate receptor antagonist.

BACKGROUND ART

Epilepsy is one of the most common central nervous system diseases, affecting over 50,000,000 or more persons throughout the world. The WHO defines it as "chronic disease of the brain of various causes, characterized by recurrent seizures (epileptic seizures) due to excessive discharge of cerebral neurons, accompanied by highly variable clinical and laboratory findings".

Examples of known types of epileptic seizures include partial seizures such as simple partial seizures, complex partial seizures and secondary generalized seizures, as well as absent seizures, myoclonic seizures, clonic seizures, tonic seizures, tonic-clonic seizures and cataplexy. The known types of intractable epilepsy include West syndrome, Lennox-Gastaut syndrome, tuberous sclerosis, Dravet syndrome and fragile X syndrome. Treatment for epilepsy is focused on drug therapy with antiepileptic drugs (AED). The goal of epilepsy drugs is to eliminate epileptic seizures while avoiding side-effects of the treatment.

Treatment using antiepileptic drugs generally begins with a single agent. Single-drug treatment will usually be carried out with 2 or 3 different types of drugs, and if found to be ineffective, it may be followed by combination therapy. About 70% of newly diagnosed epilepsy patients can expect remission of seizures with antiepileptic drug treatment. For the remaining 30% of patients, however, epileptic seizures are difficult to suppress even with combination therapy using existing drugs. A need therefore exists for development of a highly effective combination therapy.

Examples of drugs being marketed for treatment of epilepsy include carbamazepine, ethosuximide, phenobarbital, phenytoin, primidone, sodium valproate, zonisamide, felbamate, gabapentin, lamotrigine, topiramate, tiagabine, levetiracetam, oxcarbazepine, eslicarbazepine, pregabalin, lacosamide, rufmamide, trimethadione, sultiame, acetazolamide, vigabatrin, benzodiazepine-based drugs (such as clonazepam, clobazam, nitrazepam and diazepam), perampanel and retigabine (NPL 1). These existing antiepileptic drugs exhibit their effects by suppressing over-excitation of neurons.

One of the major issues in drug therapy with antiepileptic drugs is toxic symptoms (symptoms including dizziness, nystagmus, diplopia, sleepiness, vomiting, ataxia, neurologic symptoms, malaise and loss of volition) resulting from suppression of neural function.

These are side-effects that manifest in a dose-dependent manner for most conventional antiepileptic drugs, and they constituent a major problem that restricts selection and dosaging of therapeutic agents. They also significantly lower the quality of life of epilepsy patients in need of long-term use of the drugs. Reducing the dosages of the individual active ingredients in combination agents can potentially create divergence between effective doses and neurotoxic doses, thus allowing safer and more effective treatment to be provided not only for cases with resistance to the drug treatments but also for epilepsy cases in general.

Indan-1-ylsulfamide derivatives such as N-[(1 S)-2,2,5,7-tetrafluoro-2,3-dihydro-1H-inden-1-yl]sulfamide (hereunder also referred to as "compound (Ia)"), N-[(1S)-2,2,4,7-tetrafluoro-2,3-dihydro-1H-inden-1-yl]sulfamide (hereunder also referred to as "compound (Ib)") and (+)-N-(2,2,4,6,7-pentafluoro-2,3-dihydro-1H-inden-1-yl)sulfamide (hereunder also referred to as "compound (Ic)") represented by formulas (Ia), (Ib) and (Ic), respectively, have been reported to exhibit an ameliorating effect on seizure severity (score) in mouse kindling models, a type of epilepsy model, and to be useful as epilepsy treatment agents (PTL 1).

(Ia)

(Ib)

(Ic)

AMPA-type glutamate receptors play an important role in generation of epilepsy waves and their propagation through synapses. AMPA-type glutamate receptor antagonists inhibit activation of post-synaptic AMPA-type glutamate receptors by glutamate, suppressing overexcitement of nerves and reducing epileptic seizures. A large number of AMPA-type glutamate receptor antagonists have been reported to date. Of the previously mentioned drugs that are being marketed for epilepsy treatment, perampanel (3-(2-cyanophenyl)-5-(2-pyridyl)-1-phenyl-1,2-dihydropyridin-2-one) represented by chemical formula (II) (also referred to hereunder as "compound (II)") is an AMPA-type glutamate receptor antagonist.

(II)

The group of pyranodipyridine compounds including compounds represented by chemical formula (III) (hereunder also referred to as "compound (III)") also exhibit antagonism for AMPA-type glutamate receptors, and are reported to be useful as epilepsy treatment agents (PTL 2).

(III)

CITATION LIST

Patent Literature

[PTL 1] International Patent Publication No. WO2013/191144
[PTL 2] International Patent Publication No. WO2017/82288

Non-Patent Literature

[NPL 1] Shrivastava et al., "An overview on antiepileptic drugs", Drug Discoveries & Therapeutics., Vol. 6, No. 4, p. 178-193, 2012

SUMMARY OF INVENTION

Technical Problem

It is an object of the present invention to provide a combination agent that exhibits powerful anticonvulsant action and has a potential for use as a therapeutic agent for epilepsy.

Solution to Problem

In order to solve this problem, the present inventors have carried out avid investigation using a mouse sound-induced convulsion model and a rat lithium-pilocarpine status epilepticus model. As a result it has been found that combination of an indan-1-ylsulfamide derivative and an AMPA-type glutamate receptor antagonist markedly inhibits sound-induced convulsions in a mouse sound-induced convulsion model. After further research using a rat lithium-pilocarpine status epilepticus model, it was found that combination of an indan-1-ylsulfamide derivative and an AMPA-type glutamate receptor antagonist markedly inhibits status epilepticus seizures, and the invention was thereupon completed.

Specifically, the invention relates to the following <1> to <14>.
<1> A therapeutic agent for epilepsy for combined use of N-[(1S)-2,2,5,7-tetrafluoro-2,3-dihydro-1H-inden-1-yl]sulfamide (Ia)

or a pharmaceutically acceptable salt thereof, and an AMPA-type glutamate receptor antagonist.

<2> A therapeutic agent for epilepsy for simultaneous or separate administration of N-[(1S)-2,2,5,7-tetrafluoro-2,3-dihydro-1H-inden-1-yl]sulfamide

(Ia)

or a pharmaceutically acceptable salt thereof and an AMPA-type glutamate receptor antagonist.
<3> A therapeutic agent for epilepsy, comprising N-[(1S)-2,2,5,7-tetrafluoro-2,3-dihydro-1H-inden-1-yl]sulfamide

(Ia)

or a pharmaceutically acceptable salt thereof, and an AMPA-type glutamate receptor antagonist.
<4> The therapeutic agent according to any one of <1> to <3> above, wherein the AMPA-type glutamate receptor antagonist is a compound selected from the following group consisting of:
3-(2-cyanophenyl)-5-(2-pyridyl)-1-phenyl-1,2-dihydropyridin-2-one,

(II)

9-(2-chlorophenyl)-7-(pyridin-3-yl)-6H-pyrano[3,2-b:5,4-b']dipyridine-8(7H)-one,

(III)

2-fluoro-6-(7-(5-methoxypyridin-3-yl)-8-oxo-7,8-dihydro-6H-pyrano[3,2-b:5,4-b']dipyridin-9-yl)benzonitrile,

(IV)

2-fluoro-6-(7-(6-methylpyridin-3-yl)-8-oxo-7,8-dihydro-6H-pyrano[3,2-b:5,4-b']dipyridin-9-yl)benzonitrile,

(V)

9-(2-chloro-3-fluorophenyl)-7-(6-methylpyridin-3-yl)-6H-pyrano[3,2-b:5,4-b']dipyridine-8(7H)-one,

(VI)

2-fluoro-6-(7-(2-methoxypyrimidin-5-yl)-8-oxo-7,8-dihydro-6H-pyrano[3,2-b:5,4-b']dipyridin-9-yl)benzonitrile,

(VII)

7-(pyridin-3-yl)-9-(2,3,5,6-tetrafluorophenyl)-6H-pyrano[3,2-b:5,4-b']dipyridine-8(7H)-one,

(VIII)

3-(8-oxo-7-(thiophen-3-yl)-7,8-dihydro-6H-pyrano[3,2-b:5,4-b']dipyridin-9-yl)picolinonitrile

(IX)

3-(8-oxo-7-(thiophen-3-yl)-7,8-dihydro-6H-pyrano[3,2-b:5,4-b']dipyridin-9-yl)pyrazine-2-carbonitrile,

(X)

9-(2-fluorophenyl)-7-phenyl-6H-pyrano[3,2-b:5,4-b']dipyridine-8(7H)-one, (XI)

2-(7-(4-fluorophenyl-8-oxo-7,8-dihydro-6H-pyrano[3,2-b:
  5,4-b']dipyridin-9-yl)benzonitrile, (XII)

3-(7-(4-fluorophenyl)-8-oxo-7,8-dihydro-6H-pyrano[3,2-b:
  5,4-b']dipyridin-9-yl)picolinonitrile, (XIII)

3-(7-(2-fluorophenyl)-8-oxo-7,8-dihydro-6H-pyrano[3,2-b:
  5,4-b']dipyridin-9-yl)picolinonitrile, (XIV)

3-(3-fluoro-8-oxo-7-phenyl-7,8-dihydro-6H-pyrano[3,2-b:
  5,4-b']dipyridin-9-yl)picolinonitrile, (XV)

2-fluoro-6-(3-fluoro-8-oxo-7-(pyridin-3-yl)-7,8-dihydro-
  6H-pyrano[3,2-b:5,4-b']dipyridin-9-yl)benzonitrile, (XVI)

2-fluoro-6-(7-(5-fluoropyridin-3-yl)-8-oxo-7,8-dihydro-6H-
  pyrano[3,2-b:5,4-b']dipyridin-9-yl)benzonitrile, (XVII)

2-fluoro-6-(10-fluoro-3-oxo-4-(pyridin-3-yl)-4,5-dihydro-
  3H-chromeno[3,4-b]pyridin-2-yl)benzonitrile, (XVIII)

9-(2-chloro-3-fluorophenyl)-7-(5-fluoropyridin-3-yl)-6H-
  pyrano[3,2-b:5,4-b']dipyridine-8(7H)-one, (XIX)

2-fluoro-6-(8-oxo-7-(pyrimidin-5-yl)-7,8-dihydro-6H-pyrano[3,2-b:5,4-b']dipyridin-9-yl)benzonitrile, (XX)

3,6-difluoro-2-(8-oxo-7-(pyridin-3-yl)-7,8-dihydro-6H-pyrano[3,2-b:5,4-b']dipyridin-9-yl)benzonitrile, (XXI)

2-(7-(5-chloropyridin-3-yl)-8-oxo-7,8-dihydro-6H-pyrano[3,2-b:5,4-b']dipyridin-9-yl)-6-fluorobenzonitrile, (XXII)

2-fluoro-6-(7-(2-methylpyrimidin-5-yl)-8-oxo-7,8-dihydro-6H-pyrano[3,2-b:5,4-b']dipyridin-9-yl)benzonitrile, and (XXIII)

9-(3-fluoro-2-methylphenyl)-7-(pyridin-3-yl)-6H-pyrano[3,2-b:5,4-b']dipyridine-8(7H)-one

(XXIV)

or a pharmaceutically acceptable salt thereof.

<5> The therapeutic agent according to any one of <1> to <3> above, wherein the AMPA-type glutamate receptor antagonist is 3-(2-cyanophenyl)-5-(2-pyridyl)-1-phenyl-1,2-dihydropyridin-2-one (II)

or a pharmaceutically acceptable salt thereof.

<6> The therapeutic agent according to any one of <1> to <3> above, wherein the AMPA-type glutamate receptor antagonist is a compound selected from the following group consisting of:

9-(2-chlorophenyl)-7-(pyridin-3-yl)-6H-pyrano[3,2-b:5,4-b']dipyridine-8(7H)-one, (III)

2-fluoro-6-(7-(5-methoxypyridin-3-yl)-8-oxo-7,8-dihydro-6H-pyrano[3,2-b:5,4-b']dipyridin-9-yl)benzonitrile, (IV)

2-fluoro-6-(7-(6-methylpyridin-3-yl)-8-oxo-7,8-dihydro-6H-pyrano[3,2-b:5,4-b']dipyridin-9-yl)benzonitrile, (V)

9-(2-chloro-3-fluorophenyl)-7-(6-methylpyridin-3-yl)-6H-pyrano[3,2-b:5,4-b']dipyridine-8(7H)-one, (VI)

2-fluoro-6-(7-(2-methoxypyrimidin-5-yl)-8-oxo-7,8-dihydro-6H-pyrano[3,2-b:5,4-b']dipyridin-9-yl)benzonitrile, (VII)

7-(pyridin-3-yl)-9-(2,3,5,6-tetrafluorophenyl)-6H-pyrano[3,2-b:5,4-b']dipyridine-8(7H)-one, (VIII)

3-(8-oxo-7-thiophen-3-yl)-7,8-dihydro-6H-pyrano[3,2-b:5,4-b']dipyridin-9-yl)picolinonitrile (IX)

3-(8-oxo-7-(thiophen-3-yl)-7,8-dihydro-6H-pyrano[3,2-b:5,4-b']dipyridin-9-yl)pyrazine-2-carbonitrile, (X)

9-(2-fluorophenyl)-7-phenyl-6H-pyrano[3,2-b:5,4-b']dipyridine-8(7H)-one,

(XI)

2-(7-(4-fluorophenyl)-8-oxo-7,8-dihydro-6H-pyrano[3,2-b:
5,4-b']dipyridin-9-yl)benzonitrile, (XII)

3-(7-(4-fluorophenyl)-8-oxo-7,8-dihydro-6H-pyrano[3,2-b:
5,4-b']dipyridin-9-yl)picolinonitrile, (XIII)

3-(7-(2-fluorophenyl)-8-oxo-7,8-dihydro-6H-pyrano[3,2-b:
5,4-b']dipyridin-9-yl)picolinonitrile, (XIV)

3-(3-fluoro-8-oxo-7-phenyl-7,8-dihydro-6H-pyrano[3,2-b:
5,4-b']dipyridin-9-yl)picolinonitrile, (XV)

2-fluoro-6-(3-fluoro-8-oxo-7-(pyridin-3-yl)-7,8-dihydro-
6H-pyrano[3,2-b:5,4-b']dipyridin-9-yl)benzonitrile, (XVI)

2-fluoro-6-(7-(5-fluoropyridin-3-yl)-8-oxo-7,8-dihydro-6H-
pyrano[3,2-b:5,4-b']dipyridin-9-yl)benzonitrile, (XVII)

2-fluoro-6-(10-fluoro-3-oxo-4-(pyridin-3-yl)-4,5-dihydro-
3H-chromeno[3,4-b]pyridin-2-yl)benzonitrile, (XVIII)

9-(2-chloro-3-fluorophenyl)-7-(5-fluoropyridin-3-yl)-6H-
pyrano[3,2-b:5,4-b']dipyridine-8(7H)-one, (XIX)

2-fluoro-6-(8-oxo-7-(pyrimidin-5-yl)-7,8-dihydro-6H-pyrano[3,2-b:5,4-b']dipyridin-9-yl)benzonitrile, (XX)

3,6-difluoro-2-(8-oxo-7-(pyridin-3-yl)-7,8-dihydro-6H-pyrano[3,2-b:5,4-b']dipyridin-9-yl)benzonitrile, (XXI)

2-(7-(5-chloropyridin-3-yl)-8-oxo-7,8-dihydro-6H-pyrano[3,2-b:5,4-b']dipyridin-9-yl)-6-fluorobenzonitrile, (XXII)

2-fluoro-6-(7-(2-methylpyrimidin-5-yl)-8-oxo-7,8-dihydro-6H-pyrano[3,2-b:5,4-b']dipyridin-9-yl)benzonitrile, (XXIII)

and
9-(3-fluoro-2-methylphenyl)-7-(pyridin-3-yl)-6H-pyrano[3,2-b:5,4-b']dipyridine-8(7H)-one

(XXIV)

or a pharmaceutically acceptable salt thereof.

<7> The therapeutic agent according to any one of <1> to <3> above, wherein the AMPA-type glutamate receptor antagonist is 2-fluoro-6-(3-fluoro-8-oxo-7-(pyridin-3-yl)-7,8-dihydro-6H-pyrano[3,2-b:5,4-b']dipyridin-9-yl)benzonitrile

(XVI)

or a pharmaceutically acceptable salt thereof.

<8> An AMPA-type glutamate receptor antagonist for treatment of epilepsy by use in combination with N-[(1S)-2,2,5,7-tetrafluoro-2,3-dihydro-1H-inden-1-yl]sulfamide

(Ia)

or a pharmaceutically acceptable salt thereof.

<9> N-[(1S)-2,2,5,7-Tetrafluoro-2,3-dihydro-1H-inden-1-yl]sulfamide (Ia)

or a pharmaceutically acceptable salt thereof, for treatment of epilepsy by use in combination with an AMPA-type glutamate receptor antagonist.

<10> A method for treating epilepsy, for combined use of N-[(1S)-2,2,5,7-tetrafluoro-2,3-dihydro-1H-inden-1-yl]sulfamide or a pharmaceutically acceptable salt thereof, and an AMPA-type glutamate receptor antagonist.

<11> A pharmaceutical composition comprising N-[(1S)-2,2,5,7-tetrafluoro-2,3-dihydro-1H-inden-1-yl]sulfamide or a pharmaceutically acceptable salt thereof, an AMPA-type glutamate receptor antagonist, and an excipient.

<12> A kit comprising:
a pharmaceutical composition comprising N-[(1S)-2,2,5,7-tetrafluoro-2,3-dihydro-1H-inden-1-yl]sulfamide or a pharmaceutically acceptable salt thereof and an excipient, and
a pharmaceutical composition comprising an AMPA-type glutamate receptor antagonist and an excipient.

<13> Use of an AMPA-type glutamate receptor antagonist for production of a therapeutic agent for epilepsy by use in combination with N-[(1S)-2,2,5,7-tetrafluoro-2,3-dihydro-1H-inden-1-yl]sulfamide or a pharmaceutically acceptable salt thereof.

<14> Use of N-[(1S)-2,2,5,7-tetrafluoro-2,3-dihydro-1H-inden-1-yl]sulfamide or a pharmaceutically acceptable salt thereof; for production of a therapeutic agent for epilepsy by use in combination with an AMPA-type glutamate receptor antagonist.

The compounds represented by formulas (III) to (XXIV) will hereunder be referred to collectively as "compounds (III) to (XXIV)".

Advantageous Effects of Invention

The present invention provides a drug that combines an indan-1-ylsulfamide derivative and an AMPA-type glutamate receptor antagonist. The drug exhibits a more remarkable antiepileptic effect than when each of the components are used independently, and it has a potential for use as a therapeutic agent for epilepsy.

DESCRIPTION OF EMBODIMENTS

The present invention will now be explained in detail.
Compound (Ia), (Ib) or (Ic), or a pharmaceutically acceptable salt thereof, can be produced by the method described in PTL 1, for example. Compound (II) or its pharmaceutically acceptable salt can be produced by the method described in International Patent Publication No. WO2006/004100, for example. Compounds (III) to (XXIV) or their pharmaceutically acceptable salts can be produced by the method described in PTL 2, for example.

A "pharmaceutically acceptable salt" is not particularly restricted so long as it is formed with the compound of the invention, and specific examples include acid addition salts such as inorganic acid salts, organic acid salts or acidic amino acid salts.

Examples of salts with inorganic acids include salts with hydrochloric acid, hydrobromic acid, sulfuric acid, nitric acid or phosphoric acid. Examples of salts of organic acids include salts of acetic acid, succinic acid, fumaric acid, maleic acid, tartaric acid, citric acid, lactic acid, stearic acid, benzoic acid, methanesulfonic acid, ethanesulfonic acid and p-toluenesulfonic acid.

Examples of salts of acidic amino acids include salts of aspartic acid and glutamic acid.

The therapeutic agent of the invention may have compound (la), (Ib) or (Ic), or a pharmaceutically acceptable salt thereof, and an AMPA-type glutamate receptor antagonist, i.e. a compound selected from the group consisting of compound (II) and compounds (III) to (XXIV), or a pharmaceutically acceptable salt thereof, formulated separately, and both administered either simultaneously or separately. The two preparations may also be placed in a single package as a kit formulation. Both compounds may also be included in a single formulation.

The therapeutic agent of the invention can be produced by mixing pharmaceutically acceptable additives with compound (Ia), (Ib) or (Ic) or a pharmaceutically acceptable salt thereof, and/or a compound selected from the group consisting of compound (II) and compounds (III) to (XXIV) or a pharmaceutically acceptable salt thereof. The epilepsy treatment agent of the invention can be produced by a known method, such as the method described in the General Rules for Preparations of the Japanese Pharmacopoeia, 16th Edition.

The therapeutic agent of the invention may be appropriately administered to a patient as suitable for the dosage form.

The dose of compound (Ia), (Ib) or (Ic) or a pharmaceutically acceptable salt thereof in the therapeutic agent of the invention will differ depending on the severity of symptoms, the patient age, gender, body weight and sensitivity, the method and timing of administration, and the type of medical formulation, but usually the daily dose for oral administration to an adult (60 kg body weight) will be 100 µg to 5 g, or alternatively 300 µg to 3 g or yet alternatively 1 mg to 1 g, or for injected administration, 30 µg to 1 g, alternatively 30 µg to 500 mg or yet alternatively 50 µg to 300 mg, given either once or in divided portions.

The dosage of the compound selected from the group consisting of compound (II) and compounds (III) to (XXIV) or a pharmaceutically acceptable salt thereof in the therapeutic agent of the invention may be selected as appropriate, in the manner described above. For oral administration to an adult (60 kg body weight), the daily administration will usually be 10 µg to 500 mg, alternatively 30 µg to 300 mg or yet alternatively 50 µg to 100 mg, or for injected administration, 3 µg to 100 mg, alternatively 10 µg to 100 mg or yet alternatively 10 µg to 50 mg, given either once or in divided portions.

The dose of compound (Ia), (Ib) or (Ic) or a pharmaceutically acceptable salt thereof in the therapeutic agent of the invention and the dose of the compound selected from the group consisting of compound (II) and compounds (III) to (XXIV) or a pharmaceutically acceptable salt thereof, will differ depending on the severity of symptoms, the patient age, gender, body weight and sensitivity, the method and timing of administration, and the type of medical formulation. Usually, for oral administration to an adult (60 kg body weight), the daily administration of compound (Ia), (Ib) or (Ic) or a pharmaceutically acceptable salt thereof will be 100 µg to 5 g and the daily administration of the compound selected from the group consisting of compound (II) and compounds (II) to (XXIV) or a pharmaceutically acceptable salt thereof will be 10 µg to 500 mg, given orally either once or in divided portions. Alternatively, for oral administration to an adult (60 kg body weight), the daily administration of compound (Ia), (Ib) or (Ic) or a pharmaceutically acceptable salt thereof may be 300 µg to 3 g and the daily administration of the compound selected from the group consisting of compound (I) and compounds (II) to (XXIV) or a pharmaceutically acceptable salt thereof may be 30 µg to 300 mg, given either once or in divided portions. Yet alternatively, for oral administration to an adult (60 kg body weight), the daily administration of compound (Ia), (Ib) or (Ic) or a pharmaceutically acceptable salt thereof may be 1 mg to 1 g and the daily administration of the compound selected from the group consisting of compound (II) and compounds (III) to (XXIV) or a pharmaceutically acceptable salt thereof may be 50 µg to 100 mg, given either once or in divided portions. Usually, for injected administration to an adult (60 kg body weight), the daily administration of compound (a), (Ib) or (Ic) or a pharmaceutically acceptable salt thereof will be 30 µg to 1 g and the daily administration of the compound selected from the group consisting of compound (II) and compounds (I) to (XXIV) or a pharmaceutically acceptable salt thereof will be 3 µg to 100 mg, given orally either once or in divided portions. Alternatively, for injected administration to an adult (60 kg body weight), the daily administration of compound (Ia), (Ib) or (Ic) or a pharmaceutically acceptable salt thereof may be 30 µg to 500 mg and the daily administration of the compound selected from the group consisting of compound (II) and compounds (III) to (XXIV) or a pharmaceutically acceptable salt thereof will be 10 µg to 100 mg, given either once or in divided portions. Yet alternatively, for injected administration to an adult (60 kg body weight), the daily administration of compound (Ia), (Ib) or (Ic) or a pharmaceutically acceptable salt thereof may be 50 µg to 300 mg and the daily administration of the compound selected from the group consisting of compound (II) and compounds (III) to (XXIV) or a pharmaceutically acceptable salt thereof will be 10 µg to 50 mg, given either once or in divided portions.

EXAMPLES

Pharmacological Test Examples

The present inventors carried out research using a mouse sound-induced convulsion model to confirm the suppressive effects on seizures. We also conducted research using a rat lithium-pilocarpine status epilepticus model to confirm the suppressive effects against status epilepticus seizures.

[Test Example 1] Confirmation Test for Suppressive Effect Against Convulsions Using Mouse Sound-Induced Convulsion Model A mouse sound-induced convulsion model test was carried out to confirm the suppressive effect on convulsions. Tonic convulsion induced by sound stimulation is used as the index for evaluation in this model (European Journal of Pharmacology, 222, p 193-203(1992)).

<Method>

Three-week-old male DBA/2 JJcl mice (Clea Japan, Inc.) were provided for the test (n=5 for each treatment, total 2 times). Tonic convulsion induced by sound stimulation was used as the indicator for evaluation (see aforementioned publication).

Compound (Ia) and/or compound (11) was dissolved in a 0.4% methyl cellulose/5% cremophor/5% 1N hydrochloric acid/10% dimethyl sulfoxide solution for an administered dose of 20 mL/kg each to prepare samples which were orally administered. A mixed solution without the compound (vehicle) was used as a negative control. The group composition was as shown in Table 1. Sound stimulation (11 kHz, 115 dB, duration: 30 sec) was carried out 30 minutes after administration of the samples, to induce convulsions. Immediately after cessation of the sound stimulation, tonic convulsion was evaluated by observing the presence or absence of hindlimb extension. The percentage in each administered group exhibiting tonic convulsion (% Tonic convulsion) was calculated.

Based on the calculated % Tonic convulsion, the 50% effective doses for the group administered compound (Ia) alone, the group administered compound (II) alone, and the group administered a combination of compound (Ia) and compound (II) (compound (Ia) ED50, compound (II) ED50 and ED50 mix, respectively) were calculated by regression analysis. Following a method described in the literature (Epilepsia, 44, p 1003-1013(2003)), the theoretical additive ED50 value (ED50 add) was calculated and the isobologram method was used for assessment, as synergy when the ED50 mix/ED50 add ratio was less than 0.7, addition when it was 0.7 to 1.3, and antagonism when it was greater than 1.3.

<Results>

The ED50 for each administered group in the mouse sound-induced convulsion model is shown in Table 2. The theoretical additive ED50 value (ED50 add) was calculated to be 26 mg/kg. Since the result was an ED50 mix/ED50 add ratio of 0.58 (Table 3), it was demonstrated that combination of compound (Ia) and compound (II) exhibited a synergistic anti-convulsive effect. This result indicates that the drugs of the invention exhibit a remarkable suppressive effect against convulsions.

TABLE 1

| Group No. | Treatment |
| --- | --- |
| 1 | Vehicle |
| 2 | 25 mg/kg compound (Ia) |
| 3 | 50 mg/kg compound (Ia) |
| 4 | 100 mg/kg compound (Ia) |
| 5 | 200 mg/kg compound (Ia) |
| 6 | 0.125 mg/kg compound (II) |
| 7 | 0.25 mg/kg compound (II) |
| 8 | 0.5 mg/kg compound (II) |
| 9 | 1 mg/kg compound (II) |
| 10 | 7.5 mg/kg compound (Ia) + 0.05 mg/kg compound (II) |
| 11 | 15 mg/kg compound (Ia) + 0.1 mg/kg compound (II) |
| 12 | 30 mg/kg compound (Ia) + 0.2 mg/kg compound (II) |
| 13 | 60 mg/kg compound (Ia) + 0.4 mg/kg compound (II) |

TABLE 2

| Compound | ED50 |
| --- | --- |
| (Ia) | 53 mg/kg |
| (II) | 0.33 mg/kg |
| (Ia) + (II) | 15 mg/kg |

TABLE 3

| ED50mix | 15 mg/kg |
| --- | --- |
| ED50add | 26 mg/kg |
| Ratio (ED50mix/ED50add) | 0.58 |
| Assessment | Synergy |

[Test Example 2] Confirmation Test (1) for Suppressive Effect Against Status Epilepticus Seizures Using Rat Lithium-Pilocarpine Status Epilepticus Model A rat lithium-pilocarpine status epilepticus model test was conducted to confirm the suppressive effects against status epilepticus seizures. The degree of brain wave spikes induced by the drug is used as the index for evaluation in this model (Journal of Neuroscience Methods, 172, p 143-157 (2008)).

<Method>

EEG electrodes were embedded into the cranial bone under 3-component mixture anesthesia (2 mg/kg midazolam, 0.15 mg/kg medetomidine hydrochloride, 2.5 mg/kg butorphanol tartrate, subcutaneous administration). After at least 2 days of recovery following surgery, lithium chloride was administered intraperitoneally (127 mg/kg dose, 1 mLkg administered volume). After one day, pilocarpine hydrochloride (30 mg/kg dose, 5 mL/kg administered volume) and (−)-scopolaminemethyl bromide (5 mg/kg dose, 1 mL/kg administered volume) were intraperitoneally administered in a continuous manner to induce seizures. Only animals that exhibited seizures with a seizure score of 4 or higher were used for the experiment. Table 4 shows the correspondence between seizure score and symptoms. At 30 minutes after visually confirming a seizure score of 4 or higher, the vehicle or sample was administered into the caudal vein (administered volume: 1 mL/kg, injection rate: flush). The group composition was as shown in Table 5. Brain waves were recorded continuously until 1 hour after administration of the vehicle or sample. Brain wave analysis software (SleepSign by Kissei Comtec Co., Ltd., Nagano Prefecture) was used to calculate the Total power ($\mu V^2$) for each set epoch (4 seconds/epoch) from the brain wave data for each individual (analysis target frequency: ≥5 Hz, <100 Hz). After excluding epochs containing noise due to movement of the animals, the period 10 minutes before administration was targeted and the average power ($\mu V^2$) per epoch at each frequency was calculated, after which all of the frequency bands were totaled to obtain the Pre total power ($\mu V^2$) for each individual. FFT analysis was carried out for a 1 hour period after administration in the same manner, to calculate the Post total power ($\mu V^2$) for each individual. The percentage (%) of the Post total power with respect to the Pre total power ((Post total power/Pre total power)×100) was calculated for each individual, and statistical analysis was performed. Statistical significance between the vehicle group and the group administered the combination of compound (Ia) and compound (I) was determined by the unpaired t test. After one-way analysis of variance to determine the statistical significance between the group administered compound (Ia) alone and the group administered compound (II) alone, and the group administered the combination of compound (a) and compound (II), a Fisher LSD test was performed for significant cases. The significance level was considered to be 5% on both sides.

<Results>

Figure 1:
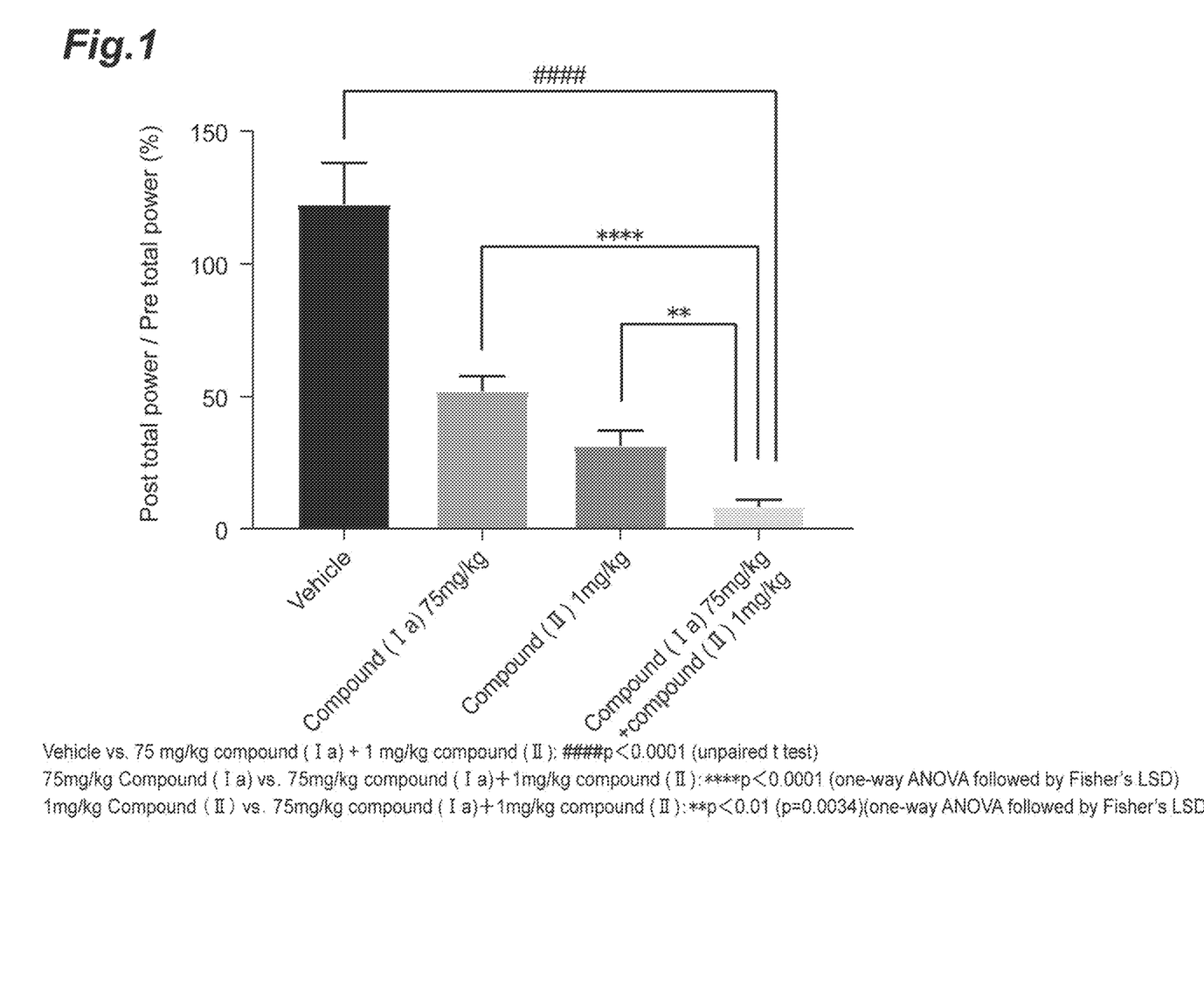
FIG. 1 shows the effect of the combination of compound (Ia) and compound (II) in a rat lithium-pilocarpine status epilepticus model, for Test Example 2.

FIG. 1 shows the effect of the combination of compound (Ia) and compound (II) in a rat lithium-pilocarpine status epilepticus model. The group given the combination of compound (Ia) and compound (II) exhibited a significant seizure-inhibitory effect compared to the vehicle group. The group given the combination of compound (Ia) and compound (II) exhibited a significant increase in seizure-inhibitory effect, even in comparison to the group given compound (Ia) alone and the group given compound (II) alone. This result demonstrates that the drugs of the invention have remarkable seizure-inhibitory effects against status epilepticus seizures.

[Test Example 3] Confirmation Test (2) for Suppressive Effect Against Status Epilepticus Seizures Using Rat Lithium-Pilocarpine Status Epilepticus Model A rat lithium-pilocarpine status epilepticus model test was conducted to confirm the suppressive effects against status epilepticus seizures.

<Method>

Six-week-old male SD rats Charles River Laboratories, Japan Inc.) were provided for the test. Lithium chloride was intraperitoneally administered (127 mg/kg dose, 1 mL/kg administered volume). After one day, pilocarpine hydrochloride (30 mg/kg dose, 5 mL/kg administered volume) and (−)-scopolaminemethyl bromide (5 mg/kg dose, 1 mL/kg administered volume) were intraperitoneally administered in a continuous manner to induce seizure. Only animals that exhibited seizure with a seizure score of 4 or higher were used for the experiment. Table 4 shows the correspondence between seizure score and symptoms. At 30 minutes after visually confirming a seizure score of 4 or higher, the vehicle or sample was administered into the caudal vein (administered volume: 1-4 mL/kg, injection rate: flush). The group composition was as shown in Table 6. Seizure was scored at 1 hour after administration of the compound, as shown in Table 4. Statistical significance between the vehicle group and the group given compound (Ia) alone, the group given compound (XVI) alone, and the group given the combination of compound (a) and compound (XVI) was determined by Holm-Sidak statistical test. Statistical significance between the group given compound (Ia) alone and the group given compound (XVI) alone, and the group given the combination of compound (Ia) and compound (XVI), was also determined by Holm-Sidak statistical test. The significance level was considered to be 5% on both sides.

<Results>

Figure 2:
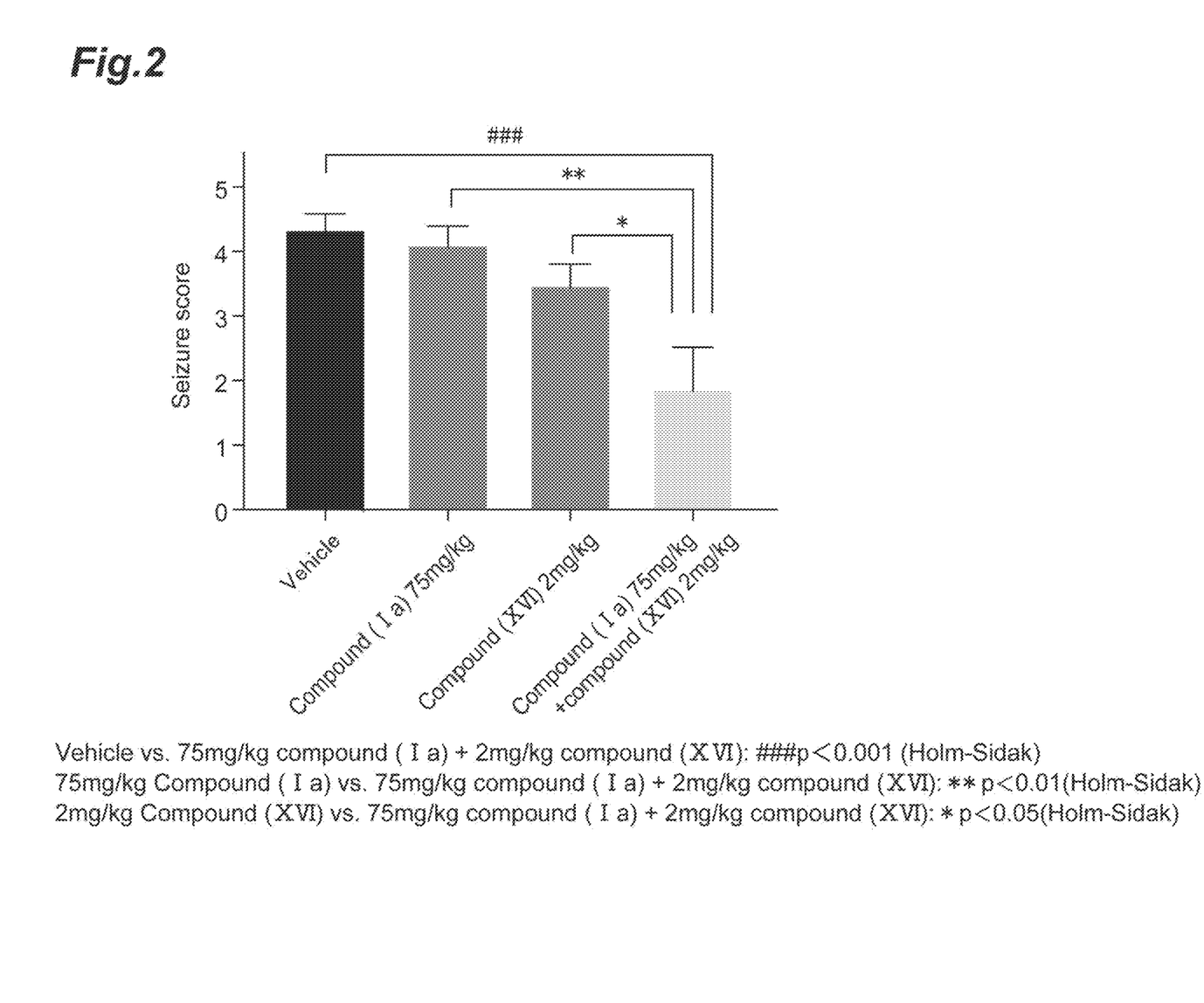
FIG. 2 shows the effect of the combination of compound (Ia) and compound (XVI) in a rat lithium-pilocarpine status epilepticus model, for Test Example 3.

FIG. 2 shows the effect of the combination of compound (Ia) and compound (XVI) in a rat lithium-pilocarpine status epilepticus model. The group given the combination of compound (a) and compound (XVI) exhibited a significant seizure-inhibitory effect compared to the vehicle group. The group given the combination of compound (a) and compound (XVI) exhibited a significant increase in seizure-inhibitory effect, even in comparison to the group given compound (Ia) alone and the group given compound (XVI) alone. This result demonstrates that the drugs of the invention have remarkable seizure-inhibitory effects against status epilepticus seizures.

TABLE 4

| Seizure score | Symptoms |
|---|---|
| 0 | No seizure |
| 1 | Mild facial clonus and blinking |
| 2 | Severe facial clonus, head bobbing, chewing |
| 3 | Unilateral or alternating forelimb clonus |
| 4 | Bilateral forelimb clonus and standing |
| 5 | Bilateral forelimb clonus with standing and falling |

TABLE 5

| Group No. | Treatment |
|---|---|
| 1 | Vehicle |
| 2 | 75 mg/kg compound (Ia) |
| 3 | 1 mg/kg compound (II) |
| 4 | 75 mg/kg compound (Ia) + 1 mg/kg compound (II) |

TABLE 6

| Group No. | Treatment |
|---|---|
| 1 | Vehicle |
| 2 | 75 mg/kg compound (Ia) |

TABLE 6-continued

| Group No. | Treatment |
|---|---|
| 3 | 2 mg/kg compound (XVI) |
| 4 | 75 mg/kg compound (Ia) + 2 mg/kg compound (XVI) |

The invention claimed is:

1. A method for treating epilepsy, comprising administering a therapeutically effective amount of N-[(1 S)-2,2,5,7-tetrafluoro-2,3-dihydro-1H-inden-1-yl]sulfamide (Ia)

or a pharmaceutically acceptable salt thereof, and 3-(2-cyanophenyl)-5-(2-pyridyl)-1-phenyl-1,2-dihydropyridin-2-one (II)

or a pharmaceutically acceptable salt thereof to a subject in need thereof.

2. The method according to claim 1, wherein N-[(1S)-2,2,5,7-tetrafluoro-2,3-dihydro-1H-inden-1-yl]sulfamide or the pharmaceutically acceptable salt thereof, and 3-(2-cyanophenyl)-5-(2-pyridyl)-1-phenyl-1,2-dihydropyridin-2-one or the pharmaceutically acceptable salt thereof are administered simultaneously.

3. The method according to claim 1, wherein N-[(1S)-2,2,5,7-tetrafluoro-2,3-dihydro-1H-inden-1-yl]sulfamide or the pharmaceutically acceptable salt thereof, and 3-(2-cyanophenyl)-5-(2-pyridyl)-1-phenyl-1,2-dihydropyridin-2-one or the pharmaceutically acceptable salt thereof are administered separately.

4. The method according to claim 1, wherein N-[(1S)-2,2,5,7-tetrafluoro-2,3-dihydro-1H-inden-1-yl]sulfamide or the pharmaceutically acceptable salt thereof, and 3-(2-cyanophenyl)-5-(2-pyridyl)-1-phenyl-1,2-dihydropyridin-2-one or the pharmaceutically acceptable salt thereof are included in a single formulation.

5. The method according to claim 1, wherein N-[(1S)-2,2,5,7-tetrafluoro-2,3-dihydro-1H-inden-1-yl]sulfamide or the pharmaceutically acceptable salt thereof, and 3-(2-cyanophenyl)-5-(2-pyridyl)-1-phenyl-1,2-dihydropyridin-2-one or the pharmaceutically acceptable salt thereof are formulated separately.

* * * * *

UNITED STATES PATENT AND TRADEMARK OFFICE
CERTIFICATE OF CORRECTION

PATENT NO. : 11,660,275 B2
APPLICATION NO. : 16/975865
DATED : May 30, 2023
INVENTOR(S) : Hiroyuki Higashiyama et al.

It is certified that error appears in the above-identified patent and that said Letters Patent is hereby corrected as shown below:

In the Claims

In Column 24, Line 9, In Claim 1, delete "(1 S)" and insert -- (1S) --.

Page 1 of 1

Signed and Sealed this
Twenty-fifth Day of July, 2023

Katherine Kelly Vidal
*Director of the United States Patent and Trademark Office*